United States Patent [19]

Sturm

[11] Patent Number: 4,582,520

[45] Date of Patent: Apr. 15, 1986

[54] METHODS AND APPARATUS FOR MEASURING AND CONTROLLING CURING OF POLYMERIC MATERIALS

[75] Inventor: Steven P. Sturm, Columbus, Ohio

[73] Assignee: Owens-Corning Fiberglas Corporation, Toledo, Ohio

[21] Appl. No.: 648,626

[22] Filed: Sep. 10, 1984

Related U.S. Application Data

[63] Continuation of Ser. No. 431,179, Sep. 30, 1982, abandoned.

[51] Int. Cl.$^4$ .......................... C03C 25/02; G01J 1/00
[52] U.S. Cl. .......................... 65/3.43; 65/4.4; 65/11.1; 65/29; 65/162; 250/339; 250/341; 250/352
[58] Field of Search ................ 65/3.1, 3.43, 4.4, 11.1, 65/29, 162; 250/339, 341, 352

[56] References Cited

U.S. PATENT DOCUMENTS

| | | |
|---|---|---|
| 3,405,268 | 10/1968 | Brunton . |
| 3,448,268 | 6/1969 | Proctor . |
| 3,524,983 | 8/1970 | Voelz . |
| 3,560,179 | 2/1971 | Kleist . |
| 3,904,876 | 9/1975 | Arendt . |
| 4,085,326 | 4/1978 | Williams . |
| 4,227,083 | 10/1980 | Sherinski . |
| 4,300,049 | 11/1982 | Sturm . |
| 4,363,968 | 12/1982 | McGowen et al. .................. 250/339 |

OTHER PUBLICATIONS

Crandall, E. W., and Jagtap, A. N., "The Near-Infrared Spectra of Polymers," *Journal of Applied Polymer Science*, vol. 21, pp. 449-454 (1977).
Brunton, D. C., "Measurement of Moisture in the Paper Industry," *Southern Pulp and Paper Manufacturer*, May 10, 1967, pp. 108, 109, 114, 116, 117.
Brunton, D. C., "On-Machine Measurement of Coating," a paper presented to the TAPPI 20th Coating Conference, Minneapolis, Minn., May 25-29, 1969.
Brunton, D. C., "Moisture and Basis Weight Measured by Infrared," *Paper Trade Journal*, Apr. 15, 1968, pp. 63 and 64.
Gardner, R. C., "Moisture/Basis Weight Infrared Gage for Paper," *Instrumentation Technology*, Jan., 1968, pp. 51-54.
Overhoff, M. W., "Infrared Gauges—Their Use, Deficiencies and Application for On-Line Control," *TAPPI*, vol. 56, No. 2, Feb. 1973, pp. 70-73.
Ealing Optics Catalog, p. 464.

(List continued on next page.)

*Primary Examiner*—Robert Lindsay
*Attorney, Agent, or Firm*—C. Henry Peterson

[57] ABSTRACT

The degree of cure of a traveling carbonaceous polymeric material (on 48), formed (at 34) from a plurality of chemical reactants (32) and subjected to a curing process (at 42 and 44) is determined by directing (with 86 and 88) into the traveling material radiations including a first infrared radiation (A1) from the group thereof adapted to selectively interact with molecular resonance vibrations at frequencies that are characteristic of respective terminal functional groups of atoms involved in reactions that take place in the material during the curing process. Also directed into the material is a second infrared radiation that is either of the kind (R) that does not exhibit substantial selective interaction with molecular resonance vibrations in the material or of the kind (A2) that is adapted to selectively interact with molecular resonance vibrations at a frequency that is characteristic of groups of atoms forming the backbones of the polymeric molecules in the material. Received (at 102) from the traveling material are radiations (148) that have interacted with the material. Produced (at 116, 118 and 122) from the received radiations are first and second responses to the first and second radiations. Produced (at 122) is a third response that is a function of the mass of the polymeric material interacting with the radiations. Produced (at 122) from the first, second and third responses is an output response (140, 82) that is correlated with the degree of cure effected by the curing process.

60 Claims, 5 Drawing Figures

OTHER PUBLICATIONS

Kendall, David H., ed., *Applied Infrared Spectroscopy*, Reinhold Publishing Corp., New York, N.Y., 1966, pp. 5 and 262–267.

Military Standardization Handbook, Glass MIL-HDBK-722 (MR), Aug. 1, 1969, pp. 30 and 31.

Van Horne, W. E., "Measurement and Control of Coextruded Coatings by Infrared"; a paper distributed at the Oct., 1974, *TAPPI Testing/Paper Synthetics Conference*, pp. 35–39.

Wu, Yao-Man and Huang, Zhi-Tang, "Study of the Curing Process for Resole-Type Phenol-Formaldehyde Resins by Infrared Spectroscopy," *Gaofenzi Tongxun*, No. 6, Dec., 1981, pp. 403–407 (translation included).

Young, R. H.; Kopf, P. W.; Salgado, O., "Curing Mechanism of Phenolic Resins", *TAPPI 1980 Paper Synthetics Conference*, pp. 229–234.

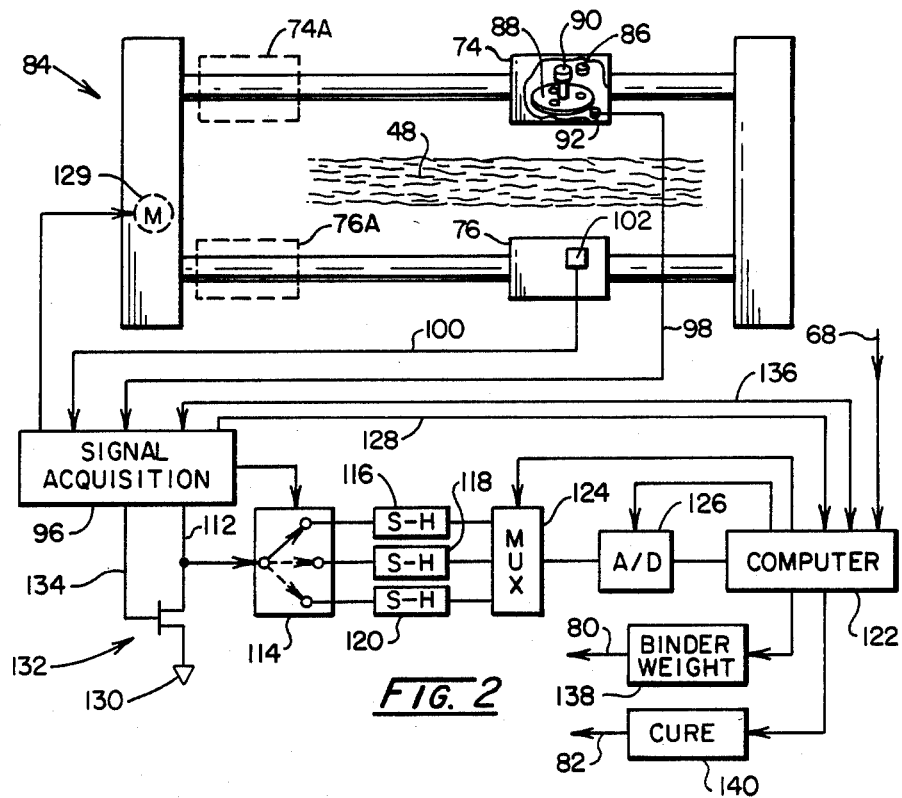

METHODS AND APPARATUS FOR MEASURING AND CONTROLLING CURING OF POLYMERIC MATERIALS

This application is a continuation of application Ser. No. 06/431,179 filed Sept. 30, 1982, now abandoned.

TECHNICAL FIELD

This invention relates to methods and apparatus for measuring and controlling the degree of cure of carbonaceous polymeric materials that are formed from a plurality of chemical reactants and passed through a curing process, from which they issue as a traveling product or intermediate in a continuous or semi-continuous form. More particularly the invention relates to methods and apparatus for performing the measurements by directing into the traveling material infrared radiations at multiple wavelengths, detecting radiations that have been transmitted or reflected by the material, and computing the degree of cure in a substantially instantaneous, continuous and non-destructive manner from instrument responses to the detected radiations.

The availability of instrumentation which functions or is constructed in accordance with the invention permits immediate manual or automatic feedback control of one or more of the process parameters that affect the degree of cure, thus enabling the manufacture of a product or intermediate in an optimized state of polymerization and with the probability of substantial raw material savings and/or energy savings.

While the methods and apparatus of the invention are applicable to the manufacture of many different polymeric material products, the invention is herein described and illustrated in an embodiment for measuring and/or controlling the degree of cure of the binder resin applied to a mat of glass fibers, to be used, for example, in building insulation products.

BACKGROUND ART

Synthetic resins and natural polymeric compounds are used in the production of a great many materials and discrete items whose manufacture includes a curing stage. The manufactured material or item may consist of the polymerized material itself, or the polymerized material may be used as a binder to hold together various layers or aggregates of other materials which in combination with the binder can impart to the finished product its desired properties.

The desired properties are often significantly affected by the degree of polymerization of the resin compound. The affected properties typically include the flexibility and toughness of plastics, or the stiffness, abrasion and impact resistance of laminated sheets.

In various manufacturing processes, the degree of polymerization has been controlled by regulating one or more process parameters such as concentration, residence time, temperature and catalysis. Various instruments have been used to determine heat liberation, viscosity, density and electrical conductivity. Spectroscopic instruments of the gas chromatographic and nuclear magnetic resonance type have been very useful. Laboratory determinations of molecular weights are commonly performed as a quality control measure.

An article by Crandall, E. W. and Jagtap, A. N., entitled "The Near-Infrared Spectra of Polymers", *Journal of Applied Polymer Science*, Vol. 21, pp. 449–454 (1977) and its bibliography have indicated that near-infrared spectroscopy can be useful in the identification of resins and polymers and in following the course of polymerization and giving some indication of the state of cure. Polymers were melted and pressed between glass plates to give a transparent film, or they were dissolved and their spectra in solution were run against the spectrum of the pure solvent. It was observed that in various polymers the process of curing (with heat) affected the relative intensities of the overtone bands of carbonyl (C=O), amino and amide N—H and alcoholic O—H. The overtone bands of alkyl and aryl C—H were also observed along with certain C—H combination bands. The intensities of various bands were set forth by way of comparison with that of the C—H stretch band whose fundamental vibration lies at 3.3–3.5 $\mu$m in the middle-infrared and whose first overtone appears at 1.7 $\mu$m in the near-infrared.

Two of the carbonaceous polymeric materials discussed by Crandall et al are phenol-formaldehyde and urea-formaldehyde resins, which are commonly utilized, inter alia, as binders in glass fiber mats, say, for building insulation. In the manufacture of these mats, typically glass fiber is spun from molten glass and is sprayed with uncured binder compound as the fiber is being showered onto a moving chain conveyor. The conveyor carries the resulting glass fiber blanket through curing ovens wherein the polymeric binder material is exposed to elevated temperatures for an appropriate time period to complete the curing of the binder. After its exit from the ovens, the mat or blanket is cooled by a stream of air from a fan, and certain of its properties may be measured, typically with radiation gauges.

The mass per unit area of the traveling mat has been measured, with various degrees of success, using beta ray gauges, gamma ray or x-ray gauges, or infrared radiation gauges using combinations of wavelengths. The resulting measurements have been used to automatically control the speed of the chain conveyor, thereby determining the amount of coated glass fibers deposited while a section of the conveyor moves through the felting chamber, with the objective of maintaining the weight per unit area of the mat constant along its length.

Various attempts have been made to measure the mass of the binder material per se, for example by taking advantage of the fact that glass is substantially transparent to certain optical (e.g., infrared) and x-ray wavelengths that are significantly attenuated by the binder materials. The objective of this measurement is to be able to control the mass of the binder by regulating the amount or the dilution of the spray material applied.

The degree of cure has been measured in laboratories, for example, by free phenol determination or molecular weight determination. On the basis of their experience with laboratory-analyzed samples, line operators typically make a visual estimate of the degree of cure by inspection of the "color" of the mat, and adjust the oven temperature accordingly. However, as an indicator of cure, color has been shown objectively to be misleading in many cases, as well as subjective. Moreover, color changes do not exhibit high sensitivity except when the mat is already over-cured (burnt).

The degree of cure of the binder is believed to have considerable economic significance, since it affects the property of the glass fiber mat which is termed "recovery". The manufactured mat is usually compressed into rolls or bales for shipment and storage, and "recovery" is the extent to which the mat is able to spring back to its original thickness when the compression is relieved. Recovery is also related to the ability of the mat to maintain its shape and thickness for long periods of time in use as insulation and for other purposes. Hence, if the binder has an optimum degree of cure, a mat with a desired thickness and insulation value in service can be manufactured from a smaller amount of glass fiber and binder. The avoidance of overcuring can also result in lower energy costs during manufacture.

The properties of recovery and resistance to sag and deterioration in service seem to be dependent on an adequate degree of polymerization. There is evidence, on the other hand, that overcuring results in depolymerization as well as other deleterious effects.

It follows that there has been a need for a method and apparatus which provides an instantaneous, substantially continuous and non-destructive indication of the degree of cure of certain traveling polymeric materials.

DISCLOSURE OF INVENTION

In accordance with this invention, there are provided methods and apparatus for determining the degree of cure of a traveling carbonaceous polymeric material that has been formed from a plurality of chemical reactants and subjected to a curing process, comprising combinations of method steps and apparatus elements for directing into the traveling material a first infrared radiation from the group thereof adapted to selectively interact with molecular resonance vibrations at frequencies that are characteristic of respective terminal functional groups of atoms involved in reactions that take place in the material during the curing process, so that the material exhibits an absorptivity for the first infrared radiation that varies with the degree of cure of the polymeric material, also directing into the traveling material a second infrared radiation that is either of the kind that does not exhibit substantial selective interaction with molecular resonance vibrations in the material or of the kind that is adapted to selectively interact with molecular resonance vibrations at a frequency that is characteristic of groups of atoms forming the backbones of the polymeric molecules in the material, receiving from the traveling material radiations that have interacted with the material; producing from the received radiations first and second responses to the first and second radiations; producing a third response that is indicative of the mass of the polymeric material interacting with the radiations, and substantially independent of the variations in the absorptivity of the material for the first infrared radiation which occur as the curing process progresses, and producing from the first, second and third responses an output response that is correlated with the degree of cure effected by the curing process.

Typically the first infrared radiation is selected from the group adapted to selectively interact with molecular resonance vibrations at respective O—H, N—H and C=O vibration frequencies.

Method steps and apparatus elements may be provided for directing into the traveling material a third infrared radiation of the other kind, producing from the received radiations a further response to the third infrared radiation, and producing the third response from the further response and the second response.

The third radiation may be adapted to selectively interact with molecular resonance vibrations at a C—H stretch vibration frequency.

The first infrared radiation may comprise the near-infrared overtone band having wavelengths in the vicinity of $1.50\mu$, whereas either of the second and third infrared radiations may have wavelengths in the vicinity of either $1.35\mu$ or $1.75\mu$.

A first mathematical function of the ratio of the first and third responses may be formed, together with a second mathematical function of the ratio of the second and third responses, and the first and second functions may be combined to produce the output response.

The first and second functions may be substantially linear functions. The ratio of the first and second functions may be formed in order to produce the output response.

The first function may be indicative of the number of terminal functional groups present in relation to the number of groups forming the backbones of the molecules, and the second function may be indicative of the number of groups forming the backbones of the molecules that have interacted with the radiations.

The first and second responses may be used to produce a fourth response that is indicative of the mass of the polymeric material interacting with the radiations but which is dependent on the variations in the absorptivity of the material for the first infrared radiation that occur as the curing process progresses, and the fourth response and the third response may be utilized to produce the output response.

The fourth response may be compensated for the radiation path length extension effects of scattering. The third response may be similarly compensated.

Method steps and apparatus elements may be provided for directing into the material further radiations having a mode of interaction that is different from that of the infrared radiations; these further radiations that have interacted with the material may be detected to produce an additional response, and the additional response may be used to effect the scattering compensation. The further radiations may be x rays or gamma rays.

The carbonaceous polymeric material may be used to form a binder coating for the fibers in a mat of glass fibers; the curing process may include exposing the mat to elevated temperatures, and the exposed mat may be passed through a measuring zone in which the radiations are directed into and received from the mat.

The exposure of the mat to the elevated temperatures may be controlled in accordance with the output responses.

The first infrared radiation may comprise a near-infrared overtone band adapted to selectively interact with molecular resonance vibrations at one or both of the O—H and N—H vibration frequencies.

Method steps and apparatus elements may be provided for measuring the weight per unit area of the mat passing through the measuring zone, and controlling the rate of travel of the mat in accordance with the weight per unit area measurement; controlling the rate of application of the binder coating in accordance with the second mathematical function, and controlling the temperature of the mat during at least a portion of the curing process in accordance with the output response.

The objects of this invention are to provide methods and apparatus for accurately and reliably measuring the degree of cure of traveling carbonaceous polymeric materials in a substantially instantaneous, continuous and non-destructive manner; to provide such methods and apparatus which make possible automatic feedback control of curing processes so as to maintain constant a desired degree of polymerization of the material; to provide such methods and apparatus that are useable when the polymeric material has been applied as a binder or coating for other materials, and to provide an improved measuring and controlling system for a glass fiber manufacturing process including binder cure control.

Other objects and advantages of the invention will become apparent in the following detailed description of some best modes for carrying out the invention, taken in conjunction with the appended drawings.

BRIEF DESCRIPTION OF THE DRAWINGS

FIG. 2 is a schematic showing, including a quasi-section on the line 2—2 of FIG. 1, of an apparatus for automatically determining the degree of cure and binder weight of the polymeric coating material.

FIG. 3 is an enlarged and more detailed schematic showing of a portion of FIG. 2.

BEST MODES FOR CARRYING OUT THE INVENTION

Figure 1:
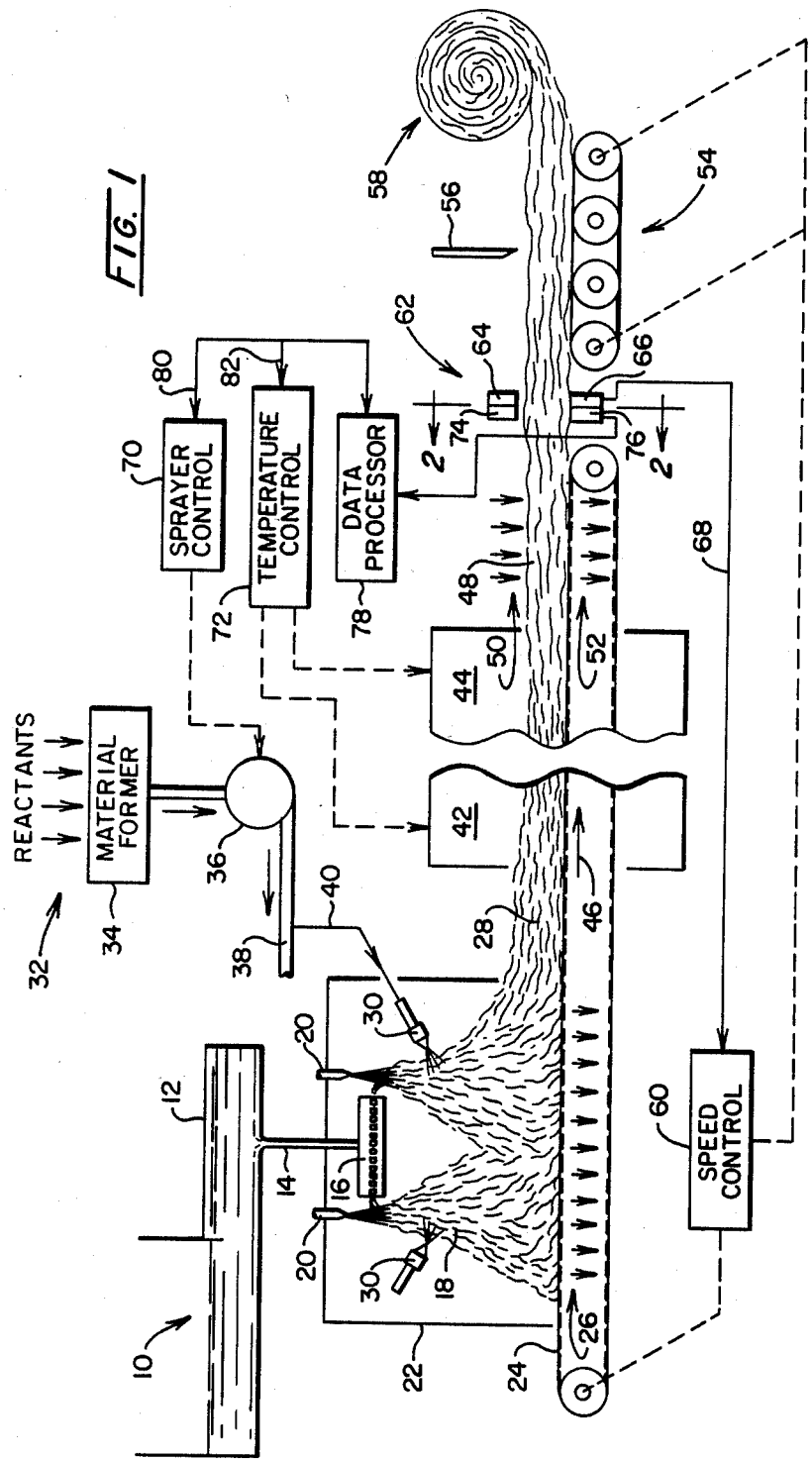
FIG. 1 is a schematic showing of a process for producing a mat of glass fibers that are coated with a controlled amount of a carbonaceous polymeric binder material and cured to an optimum degree of polymerization of the binder by a method and apparatus according to the invention.

Referring to FIG. 1, molten glass from a melter 10 flows into a forehearth 12 that supplies a stream 14 of melted glass to a centrifugal spinner 16. Filaments 18 of glass ejected from the spinner 16 are directed downwardly and partially solidified by air streams from jets as at 20. The filaments 18 descend through a felting chamber 22 and are collected on a traveling conveyor chain 24. Air suction through the conveyor 24, depicted by arrows 26, aids the formation of a fiber blanket 28 on the conveyor.

The filaments 18 are sprayed, during their descent through the felting chamber 22, with a binder spray ejected through a plurality of spray nozzles as at 30. The binder spray comprises a carbonaceous polymeric material that has been formed from a plurality of chemical reactants 32. Typically the reactants 32 comprise the components of phenol-formaldehyde and urea-formaldehyde that are mixed in a suitable material former 34 and supplied to an injection pump 36. Pump 36 pressure-feeds the spray nozzle 30 through a header 38 and distributor pipes as at 40. As a result of the foregoing process, the blanket 28 comprises a mat of glass fibers that have a binder coating of uncured carbonaceous polymeric material.

The polymeric binder material is subjected to a curing process which is completed by transporting the blanket 28 through ovens as at 42 and 44 on the conveyor 24. The conveyor moves to the right in FIG. 1, as indicated by the arrow 46. In the ovens 42 and 44, the mat of glass fibers is exposed to elevated temperatures for a time period appropriate to effect the cure of the polymeric material that forms the binder coating on the fibers.

In due time the cured glass fiber mat 48 emerges from the last oven 44 and is cooled by a current of air (indicated by arrows at 50 and 52) from a fan (not shown). The mat 48 is picked up by other conveyors indicated generally at 54 whose movement is synchronized with the operation of a shear 56 and a windup 58 that forms somewhat compressed rolls of the glass fiber mat for shipment or storage.

The filamentary glass 18 is commonly ejected from the spinner 16 at a substantially constant rate (mass per unit time) and hence the weight (mass per unit area) of the cured mat 48 depends on the rate of travel of the chain conveyor 24 as set by a conveyor speed control 60. The cured and cooled mat is commonly measured in a measuring zone 62 wherein there is located a gamma-ray or x-ray gauge having a radiation source unit 64 and a radiation detector unit 66. Radiations emitted from the source unit 64 pass through the mat 48 and are attenuated by absorption in the mat in accordance with its mass per unit area. The unabsorbed radiation is detected in the detector unit 66 to produce a detector signal that is processed by conventional means not shown to produce a response, represented by a line 68, that is utilized by the speed control unit 60 to control the speed of conveyor 24. The objective of this feedback control is to maintain the weight of the mat 48 nominally constant along its length at a desired value.

The weight (mass per unit area) of the polymeric binder material contained in the cured mat 48 is controlled by a sprayer control device 70. Device 70 may regulate the volume per unit time of the spray material fed by the pump 36 to the spray nozzles 30, or it may control the dilution of the spray material.

The degree of polymerization, or degree of cure, of the carbonaceous polymeric binder material is determined by the temperature in the ovens as at 42 and 44. The temperature of one or more of the ovens may be controlled by a temperature control unit 72. As previously noted above, the line operator commonly observes the "color" of the mat 48 issuing from the last oven 44 and manually adjusts the set-point of the temperature control unit 72 accordingly.

The apparatus so far described in connection with FIG. 1 is conventional, and no further explanation is deemed necessary. Insofar as the present invention is physically embodied in the FIG. 1 apparatus, it comprises essentially the structure of an infrared radiation gauging device in the measuring zone 62 including a source unit 74 and a detector unit 76, and a data processor arrangement 78. The data processor 78 may automatically provide set-point values, or target values, to the sprayer control device 70 and/or the oven temperature control device 72, as indicated by the respective arrowheads 80 and 82.

Referring to FIG. 2, the infrared source unit 74 and detector unit 76 are mounted on a scanner bracket assembly 84 which permits the units 74 and 76 to traverse back and forth across the width of the coated and cured glass fiber mat 48. The units 74 and 76 are also movable to off-sheet positions at 74A and 76A wherein radiations can pass from the source unit 74A to the detector unit 76A without passing through the mat 48. In this view (FIG. 2) it is assumed that the mat 48 is traveling out of the paper, toward the observer.

The infrared source unit 74 contains a radiation source means 86 and a filter wheel 88 that is rotated by a motor 90. FIG. 3 includes an enlarged showing of the filter wheel 88 and source means 86. FIG. 2 shows a magnetic reluctance sensor 92 (or other appropriate sensor) which detects the passing of small iron "logic slugs" as shown at 94 in FIG. 3 (or other appropriate indicia). A signal acquisition system 96 (FIG. 2) connected via line 98 to sensor 92 uses electrical pulses from the sensor to maintain continually updated information on the instantaneous position of the filter wheel 88. The signal acquisition system 96 is also connected via line 100 to an infrared radiation detector 102 in detector unit 76.

The signal acquisition system 96 is a conventional arrangement that is described in more detail in U.S. Pat. Nos. 4,085,326 and 4,300,049. Accordingly, the disclosure herein shows and describes only those details necessary to permit the present invention to be readily understood.

According to the terminology of U.S. Pat. No. 4,300,049, the signal acquisition system 96 contains a combination of filter wheel logic and mode switch logic. Filter wheel logic refers to the identification and routing of signals from the detector 102 according to the angular positions of the filter wheel 88 when the signals are generated.

As best shown in FIG. 3, the filter wheel 88 contains three filters: 104, 108, and 110. In the embodiment of the present invention, the filter 104 is termed a reference wavelength filter. Filters 108 and 110 are different from each other and different from filter 104, and are termed absorption wavelength filters. As filter wheel 88 rotates, the detector 102 receives pulses of radiation that have passed respectively through the three filters in sequence.

In response to the detector output, the signal acquisition system 96 delivers suitably amplified and processed signal pulses to a line 112. In response to the pulses from sensor 92, the signal acquisition system 96 operates an electronic switching arrangement 114 that routes each of the pulses on line 112 to the proper one of a group of sample-and-hold circuits 116, 118 and 120.

Accordingly, the output of circuit 116 will provide a voltage that indicates the intensity of the radiation detected after passing through the reference wavelength filter 104; the voltage output of circuit 118 will indicate the intensity of radiation detected after passing through the first absorption wavelength filter 108, and the output of circuit 120 will indicate the intensity of radiation detected after passing through the second absorption wavelength filter 110.

The circuits 116, 118 and 120 hold each of their respective, successive reference and absorption voltage outputs for a period of time somewhat less than one full revolution time of the filter wheel 88. Hence, the voltage outputs of circuits 116, 118 and 120 are made available to be "read" at convenient times by a computer 122.

The computer 122 normally reads the voltages sequentially, controlling the operation of a multiplexer 124 and analog-to-digital converter 126 and storing the numerical values obtained. Since the sample-and-hold circuit output voltages are updated every revolution of filter wheel 88, the signal acquisition system 96 keeps the computer 122 informed, by flag signals fed over a line 128, as to when the respective sample-and-hold outputs are not available to be read.

"Mode switch logic" as contained in the signal acquisition system 96 refers to the identification and routing of signals from the detector 102 according to whether the infrared radiation gauging instrument is operating in a measuring mode or a standardizing mode. In the measuring mode, the source unit 74 and detector unit 76 are positioned with the glass fiber mat 48 therebetween, so that the infrared radiation reaching the detector 102 has interacted with the material in the mat 48. In the standardizing mode, the source unit and detector unit are driven by a motor 129 to their off-sheet positions at 74A and 76A clear of the mat 48 so that the infrared radiation reaching the detector 102 has not interacted with the material in the mat. Operation in the standardizing mode allows the computer 102 to read unattenuated values for each of the detected radiations transmitted by filters 104, 108 and 110, for comparison with the corresponding measuring values that are read when the radiations are passing through the mat 48.

Because each processed pulse signal from detector 102 must be individually integrated, analog signal processing of these pulses is preferably used in the signal acquisition system 96. This avoids the need for a high speed analog-to-digital converter and eliminates a great many digital computations that would otherwise be needed for carrying out the integrations.

The sample-and-hold circuits 116, 118 and 120, used for short term storage of the integrated analog signal values, and other analog signal processing elements are prone to develop extraneous signal components. Accordingly, the extraneous signal values per se are read by the computer 122 in an offset mode of operation that is carried out at convenient times while the signals on line 112 are clamped to ground 130, as depicted in FIG. 2 by a transistor switch 132 controlled by a signal on line 134 from the signal acquisition system 96.

Computer 122 is kept informed by flag signals fed over multichannel line 128, whether the system is in the measuring mode, the standardizing mode, or the offset mode. In turn, the computer 122 may exert supervisory control over the operation of the signal acquisition system 96 as indicated by control signal line 136. For example, the computer may determine appropriate times for the gauging heads 74 and 76 to go off sheet to carry out standardization.

By operation of the FIG. 2 apparatus as described, the computer 122 receives, identifies and stores numerical responses, corresponding to infrared radiations received by the detector 102, as described in Table 1.

TABLE 1

| VALUE | MODE | FILTER | WAVELENGTH (microns) |
|---|---|---|---|
| A1 | Meas. | 108 | 1.50 |
| A2 | Meas. | 110 | 1.75 |
| R | Meas. | 104 | 1.35 |
| A1 (AIR) | Stdz. | 108 | 1.50 |
| A2 (AIR) | Stdz. | 110 | 1.75 |
| R (AIR) | Stdz. | 104 | 1.35 |
| OFF A1 | Offset | 108 | 1.50 |
| OFF A2 | Offset | 110 | 1.75 |
| OFF R | Offset | 104 | 1.37 |

The first column of Table 1 identifies the response value; the second column indicates whether the response value is derived in the measuring (Meas.), standardizing (Stdz.), or Offset mode; the third column indicates the filter interposed between the source means 86 and the detector 102, and the fourth column indicates the nominal wavelength passed by the respective filter (a narrow band interference filter).

The computer 122 also receives, as suggested by a connection to line 68, a response value WT indicative of the weight (mass per unit area) of the total mat 48 as measured by an isotopic x-ray gauge 66 (FIG. 1). The response value WT is actually derived by conventional means, including the x-ray detector head 66 and computer 122, that per se form no part of the present invention.

The memory of computer 122 contains stored constant values for several parameters designated by the alphabetical letters A through H and the Greek letter δ, as identified below.

Utilizing the stored values, computer 122 forms mathematical functions of the ratio of the A1 and R responses as follows:

$$\text{Ratio 1} = \left[ \frac{R'}{A2'} * KS1 \right] - 1 \quad (1)$$

$$L \text{ Ratio 1} = \frac{\text{Ratio 1}}{1 + \delta 1 * \text{Ratio 1}} \quad (2)$$

Likewise, the computer forms mathematical functions of the ratio of the A2 and A1 responses as follows:

$$\text{Ratio 2} = \left[ \frac{A1'}{A2'} * KS2 \right] - 1 \quad (3)$$

$$L \text{ Ratio 2} = \frac{\text{Ratio 2}}{1 + \delta 2 * \text{Ratio 2}} \quad (4)$$

In equations (1) to (4), $$R' = R - \text{OFF} R, \quad A1' = A1 - \text{OFF} A1,$$

$$KS1 = \frac{A2 \text{ (AIR)} - \text{OFF } A2}{R \text{ (AIR)} - \text{OFF } R}$$

$$KS2 = \frac{A2 \text{ (AIR)} - \text{OFF } A2}{A1 \text{ (AIR)} - \text{OFF } A1}$$

δ1 and δ2 are linearization factors, and L RATIO 1 and L RATIO 2 are substantially linear functions of the respective ratios. δ1 and δ2 are usually the same, but not necessarily so.

"Binder weight" is computed from $$\text{Binder weight} = \frac{L \text{ Ratio 1}}{A * WT + B} + [C * WT + D] \quad (5)$$

"Binder weight" is a computed response indicative of the total mass per unit area of the polymeric coating on the glass fibers in the cured mat 48. This response is used to provide a display or recording at 138, FIG. 2. It is also the basis for the control signal 80 for the sprayer control 70, FIG. 1. This response is almost completely insensitive to the degree of cure of the binder.

It is obvious that any remaining effect of degree of cure in equation (5) could be removed by cross compensation with equation (6). The method is essentially a solution of simultaneous equations, since both equations (5) and (6) are linear responses to binder weight.

Also computed is "cure weight":

$$\text{Cure weight} = \frac{L \text{ Ratio 2}}{A' * WT + B'} + [E * WT + F] \quad (6)$$

"Cure weight" is proportional to binder weight but is highly sensitive to the degree of cure.

In equations (5) and (6), the constants A, A', B and B' are used with the isotopic x-ray gauge signal WT to provide first order compensation for the radiation path length extension effects of scattering, a phenomenon whose basics are discussed in an article by Overhoff, M. W., "Infrared Gauges-Their Use, Deficiencies and Applications for On-Line Control", *TAPPI*, Vol. 56, No. 2, February 1973, pp. 70–73. A and A' are usually the same, as are B and B', but not necessarily so.

The constants C, D, E, and F provide first order compensation for the spectral effects of glass on the cure weight and binder weight measurements. The silica sand, from different sources, used in glass manufacture, may have different amounts in particular of iron oxide ($Fe^{++}$), whose effects are noted in the wave bands of interest. The effects are not the same in the cure weight and binder weight channels.

An output response that is correlated with the degree of cure is produced by combining the binder weight function and the cure weight function, in particular by forming their ratio according to:

$$\text{Cure} = \left[ \frac{\text{Cure Weight}}{\text{Binder Weight}} * G \right] + H \quad (7)$$

Here G and H are constants used to scale the cure signal into any reasonable units. At this time no industry-accepted units exist, so a calibration is provided in arbitrary units from zero to one hundred. Zero designates "uncured" material that has been heated at low temperature for a time in order to drive off moisture, whereas one hundred designates material that has been heated at a high temperature for a time so that it is definitely "overcured".

"Cure" is a computed response that is indicative of the degree of cure, or degree of polymerization, but is substantially independent of the weight or density of the glass fiber mat 48 and the weight per unit area of binder. This response is displayed or recorded at 140, FIG. 2, and provides the basis for the control device 72, FIG. 1, to control the temperature of the ovens 42 and 44.

Figure 4:
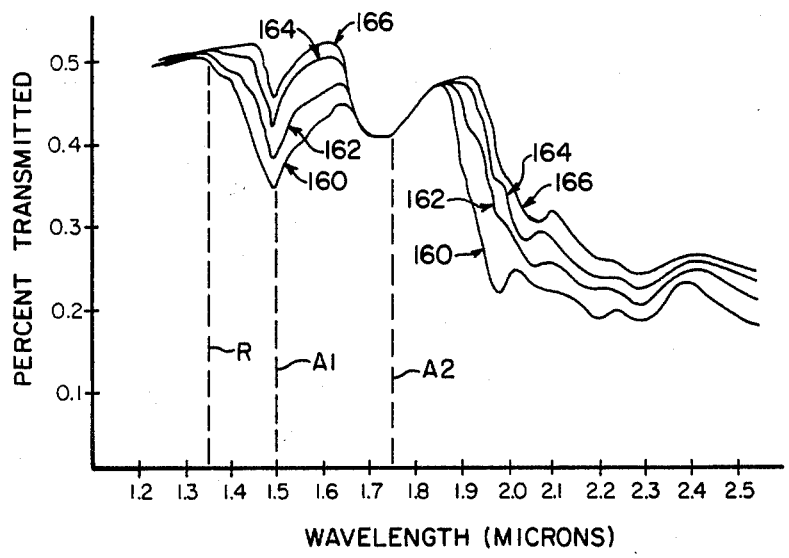
FIG. 4 is a graph depicting near-infrared absorption spectra of a particular carbonaceous polymeric material in four different stages of cure.

FIG. 4 shows infrared transmission curves for glass fiber mat of about 500 grams per square meter, coated with about 50 grams per square meter of the mat, of carbonaceous polymeric binder material, in four different stages of cure. While these curves resemble conventional spectrometer traces, it is to be noted that the maximum transmission is only about 0.5 percent. Accordingly, my commercial spectrometer was unable to provide any useful signals. Hence, data for the FIG. 4 curves was derived using apparatus similar to that illustrated in FIGS. 2 and 3. Eighteen different narrow band interference filters were used to derive data points for each curve. The curves were then sketched in by hand to show how I believe they would appear if the continuous spectra could be measured and if the absorption spectrum effects of glass were normalized.

Curve 160 is believed to be typical of the coated mat 28 that has been heated for one hour at 175° F. to drive off moisture but is essentially "uncured". Curve 162 indicates that substantial curing took place when the sample was heated at 300° F. for ten minutes. Substantial further curing took place when the sample was heated at 370° F. for 1.5 hours (curve 164). After ten minutes at 450° F. (curve 166), the sample was definitely overcured.

As is well known, for example, from Kendall, David N., Ed., *Applied Infrared Spectroscopy*, Reinhold Publishing Corp., New York, N.Y., 1966, pp. 5 and 262-267, the power P transmitted by a beam of infrared radiation passing through a material is given by $$P = P_o e^{-abc} \qquad (8)$$

where $P_o$ is the power incident on the material, a is the absorptivity, or inherent absorbing power of the material at a specific wavelength, b is the thickness or path length through the sample, and c is the density or concentration of the material.

However, as appears for example from the discussion in Kendall particularly of the spectroscopy of polymeric materials, at certain infrared wavelengths especially the absorptivity of certain materials undergoing chemical and/or physical changes is not constant, but depends on the instantaneous chemical and/or physical state of the material.

The change in the absorptivity of the polymeric binder material as curing progresses is believed to be clearly apparent from FIG. 4, especially at the A1 (1.5μ) wavelength. Hence the instructional value of the curves shown appears to justify the arduousness of their preparation.

The method and apparatus of the present invention is adapted to produce an output response to the changes in the absorptivity a of the material. At the same time, to the extent possible, the output response is made substantially independent of the amount of the polymeric material as represented by the product bc of the overall thickness and density of the material.

The practice of the present invention requires directing into the traveling material a first infrared radiation from the group thereof adapted to selectively interact with molecular resonance vibrations at frequencies that are characteristic of respective terminal functional groups of atoms involved in reactions that take place in the material during the curing process. This group of radiations includes a wavelength corresponding to the fundamental vibration frequency that commonly lies in the middle-infrared, the first overtone band that commonly lies in the near-infrared, certain combination bands, and possibly other harmonically related wavelengths.

The terminal functional groups of atoms involved in reactions that take place during the cure of the most common polymeric materials are apparently those identified in the Crandall et al article supra, namely the O—H, N—H and C═O groups.

For the glass fiber mat binder cure measurement, the first infrared radiation selected is the first overtone band in the vicinity of 1.50μ. This band is apparently adapted to selectively interact with molecular resonance vibrations at frequencies characteristic of both the O—H and the N—H terminal functional groups of atoms. While the nominal wavelength selected for filter 108 appears to be somewhat longer than the O—H and N—H overtone bands seen by Crandall et al., for example, it is noted that the apparatus of FIG. 3 is an efficient geometry wherein rays from an incandescent filament 142 are collected by a reflector 144 and directed through the filters. Similarly, rays as at 148 penetrating the mat 48 at divergent angles are collected by a reflector 146 and focused on the detector 102. As is well known, a narrow band interference filter exhibits a different pass band for rays passing through at an angle than it does for normal rays. For this and probably other reasons, the infrared band described herein is probably closer to those seen by Crandall et al. than it appears to be.

While the carbonyl (C═O) band just above 1.9μ is sensitive to cure, it is not preferred for the particular binder measurement described because of its proximity to the moisture absorption band.

The practice of the present invention also requires directing into the traveling material a second infrared radiation that is either of the kind that does not exhibit substantial selective interaction with molecular resonance vibrations in the material (e.g., the band in the vicinity of 1.35μ, FIG. 4) or of the kind that is adapted to selectively interact with molecular resonance vibrations at a frequency that is characteristic of groups of atoms forming the backbones (using the terminology of Crandall et al.) of the polymeric molecules in the material (e.g., the overtone band in the vicinity of 1.75μ, FIG. 4). The group of atoms forming the backbones in the present example, as in most cases, is the C—H group whose fundamental stretch band lies at around 3.4μ in the middle-infrared.

It is interesting to note that Crandall et al. observed an O—H stretch band at 1.34μ in urea-formaldehyde resin, which band disappeared on heat curing. However, as appears from FIG. 4, in the combination urea-formaldehyde and phenol-formaldehyde resin of the present example, at least for purposes of the binder cure measurement and binder weight measurement, the 1.35μ radiation does not exhibit substantial selective interaction with molecular resonance vibrations in the material.

The 1.75μ band is absorbed in the binder material in a manner that is substantially independent of the effects of cure, as appears from FIG. 4. Hence, the ratio of the instrument responses, as in equation (1), to the 1.35μ and 1.75μ bands provides a response that is a function of the mass of the polymeric material interacting with the radiations, and the x-ray mass signal response WT compensations should not be necessary except for the complications presented by the glass fiber structure (path extension effects of scatter) and the spectral effects of the glass composition.

It now becomes apparent also that a ratio of the instrument response to the 1.50μ band can be formed with the instrument response to either the 1.35μ band or the 1.75μ band in order to provide a response that is proportional to binder weight and highly sensitive to cure. Again, the gamma ray gauge response WT as in equation (6) should not be necessary except for the complications introduced by the glass fiber structure and composition. Such a "cure weight" response can be combined with a mass response representing the mass of the polymeric material to produce a "cure" response, and the mass response can be derived either from the ratio of the instrument response to the 1.35μ and 1.75μ bands, from the differential response of two gamma ray weight gauges operating at different energies, or from some other kind of binder mass determination.

Figure 5:
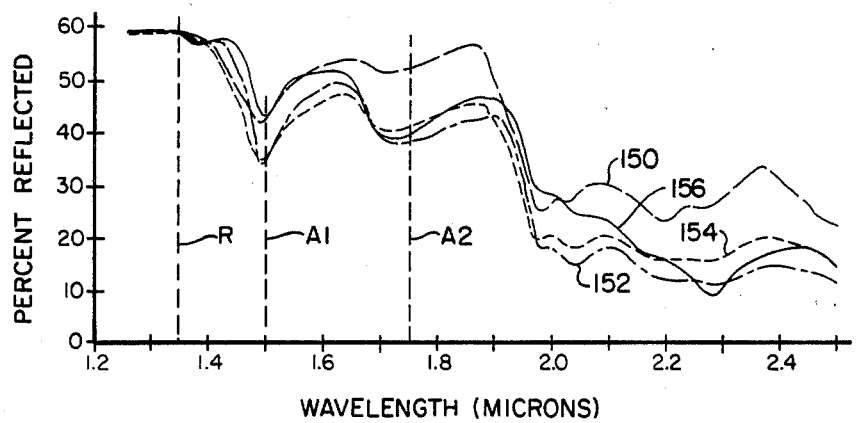
FIG. 5 is a graph depicting near-infrared reflection spectra of a particular carbonaceous polymeric material in four different stages of cure.

FIG. 5 shows reflection curves derived from commercial spectrometer traces. A quantity of polymeric binder material, of the kind that is sprayed onto the glass fibers 18 at 30, was deposited instead on a flat aluminum plate and heated at 145° F. for more than an hour to drive off moisture and other volatile components. The remaining material is termed "uncured" binder, and its reflection spectrum is drawn at 150 (the long-dashed curve). The short-dashed curve 154 was derived from the sample heated at 300° F. for a half hour. The short-dash long-dash curve 152 was derived from the sample heated at 340° F. for ten minutes. The solid curve 156 was derived from the sample heated at 450° F. for ten minutes.

The possibility of making a cure measurement by a near-infrared reflection technique is demonstrated by the fact that at certain wavelengths, in particular the 1.48μ and 1.72μ bands, the reflected intensity changes in opposite directions with different degrees of cure. For the reasons set forth hereinabove, the 1.50μ and 1.75μ filters (A1 and A2 as shown) would be appropriate. From this particular laboratory test data, a ratio of the A2 and R responses cannot provide a quantitative measurement of the mass of the polymeric material that has interacted with the radiations. However, the ratio of these responses can be correlated with the percent of binder when the binder is applied to the glass fibers using the normal process. In this case the ratio could be used along with the A2 and A1 ratio to provide quantitative measurement of degree of cure by reflection.

While the invention has been described and illustrated in the form of particular procedures and particular apparatus, the showing and description are illustrative only and not restrictive, since many changes and modifications can obviously be made without departing from the spirit and scope of the invention.

What is claimed is:

1. A method for determining the degree of cure of a traveling carbonaceous polymeric material that has been formed from a plurality of chemical reactants and subjected to a curing process, the method comprising
    directing into the traveling material a first infrared radiation from the group thereof adapted to selectively interact with molecular resonance vibrations at frequencies that are characteristic of respective terminal functional groups of atoms involved in reactions that take place in the material during the curing process, so that the material exhibits an absorptivity for the first infrared radiation that varies with the degree of cure of the polymeric material,
    also directing into the traveling material a second infrared radiation that is either of the kind that does not exhibit substantial selective interaction with molecular resonance vibrations in the material or of the kind that is adapted to selectively interact with molecular resonance vibrations at a frequency that is characteristic of groups of atoms forming the backbones of the polymeric molecules in the material, so that the material exhibits a relatively constant absorptivity for the second infrared radiation as the curing process progresses,
    receiving from the traveling material radiations that have interacted with the material,
    producing from the received radiations first and second responses to the first and second radiations,
    producing a third response that is indicative of the mass of the polymeric material interacting with the radiations and substantially independent of the variations in the absorptivity of the material for the first infrared radiation which occur as the curing process progresses, and
    producing from the first, second and third responses an output response that is a function of the changes in the absorptivity of the material for the first infrared radiation, substantially independent of the amount of the polymeric material interacting with the radiations, and correlated with the degree of cure effected by the curing process.

2. A method as in claim 1 wherein the first infrared radiation is selected from the group adapted to selectively interact with molecular resonance vibrations at respective O—H, N—H and C=O vibration frequencies.

3. A method as in claim 1 or claim 2 which comprises directing into the traveling material a third infrared radiation of the other kind,
    producing from the received radiations a further response to the third infrared radiation, and
    producing the third response from the further response and the second response.

4. A method as in claim 3 wherein the third radiation is adapted to selectively interact with molecular resonance vibrations at a C—H stretch vibration frequency.

5. A method as in claim 3 wherein the first, second and third infrared radiations comprise near-infrared overtone bands, the first radiation having wavelengths in the vicinity of 1.50μ, with either of the second and third radiations having wavelengths in the vicinity of either 1.35μ or 1.75μ.

6. A method as in claim 3 which comprises forming a first mathematical function of the ratio of the first and third responses,
    forming a second mathematical function of the ratio of the second and third responses, and
    combining the first and second functions to produce the output response.

7. A method as in claim 6 wherein the first and second functions are substantially linear functions.

8. A method as in claim 7 wherein the ratio of the first and second functions is formed in order to produce the output response.

9. A method as in claim 6 wherein the first function is indicative of the number of terminal functional groups present in relation to the number of groups forming the backbones of the molecules, and
    wherein the second function is indicative of the number of groups forming the backbones of the molecules that have interacted with the radiations.

10. A method as in claim 1 wherein the carbonaceous polymeric material is used to form a binder coating for the fibers in a mat of glass fibers,
    wherein the curing process includes exposing the mat to elevated temperatures, and
    wherein the exposed mat is passed through a measuring zone in which the radiations are directed into and received from the mat.

11. A method as in claim 10 which comprises controlling the exposure of the mat to the elevated temperatures in accordance with the output response.

12. A method as in claim 10 wherein the first infrared radiation comprises a near-infrared overtone band adapted to selectively interact with molecular resonance vibrations at one or both of the O—H and N—H vibration frequencies.

13. A method as in claim 12 wherein the first infrared radiation has wavelengths in the vicinity of 1.50μ, and the second infrared radiation has wavelengths in the vicinity of 1.35μ or 1.75μ.

14. A method as in claim 12 or claim 13 which comprises directing into the mat a third infrared radiation which is different from the second radiation and which lies in a band of wavelengths in the vicinity of 1.35μ or 1.75μ, producing from the received radiations a further response to the third infrared radiation, and producing the third response from the further response and the second response.

15. A method as in claim 14 which comprises forming a first mathematical function of the ratio of the first and third responses, forming a second mathematical function of the ratio of the second and third responses, and combining the first and second functions to produce the output response.

16. A method as in claim 15 wherein the first and second functions are substantially linear functions.

17. A method as in claim 16 wherein the ratio of the first and second functions is formed in order to produce the output response.

18. A method as in claim 15 which comprises measuring the weight per unit area of the mat passing through the measuring zone, and controlling the rate of travel of the mat in accordance with the weight per unit area measurement, controlling the rate of application of the binder coating in accordance with the second mathematical function, and controlling the temperature of the mat during at least a portion of the curing process in accordance with the output response.

19. Apparatus for determining the degree of cure of a traveling carbonaceous polymeric material that has been formed from a plurality of chemical reactants and subjected to a curing process, comprising means for directing into the traveling material a first infrared radiation from the group thereof adapted to selectively interact with molecular resonance vibrations at frequencies that are characteristic of respective terminal functional groups of atoms involved in reactions that take place in the material during the curing process, so that the material exhibits an absorptivity for the first infrared radiation that varies with the degree of cure of the polymeric material, means for directing into the traveling material a second infrared radiation that is either of the kind that does not exhibit substantial selective interaction with molecular resonance vibrations in the material or of the kind that is adapted to selectively interact with molecular resonance vibrations at a frequency that is characteristic of groups of atoms forming the backbones of the polymeric molecules in the material, so that the material exhibits a relatively constant absorptivity for the second infrared radiation as the curing process progresses, means for receiving from the traveling material radiations that have interacted with the material, means for producing from the received radiations first and second responses to the first and second radiations, means for producing a third response that is indicative of the mass of the polymeric material interacting with the radiations and substantially independent of the variations in the absorptivity of the material for the first infrared radiation which occur as the curing process progresses, and means for producing from the first, second and third responses an output response that is a function of the changes in the absorptivity of the material for the first infrared radiation, substantially independent of the amount of the polymeric material interacting with the radiations, and correlated with the degree of cure effected by the curing process.

20. Apparatus as in claim 19 wherein the first infrared radiais selected from the group adapted to selectively interact with molecular resonance vibrations at respective O—H, N—H and C=O vibration frequencies.

21. Apparatus as in claim 19 or claim 20 which comprises means for directing into the traveling material a third infrared radiation of the other kind, means for producing from the received radiations a further response to the third infrared radiation, and means for producing the third response from the further response and the second response.

22. Apparatus as in claim 21 wherein the third radiation is adapted to selectively interact with molecular resonance vibrations at a C—H stretch vibration frequency.

23. Apparatus as in claim 21 wherein the first, second and third infrared radiations comprise near-infrared overtone bands, the first radiation having wavelengths in the vicinity of $1.50\mu$, with either of the second and third radiations having wavelengths in the vicinity of either $1.35\mu$ or $1.75\mu$.

24. Apparatus as in claim 21 which comprises means for forming a first mathematical function of the ratio of the first and third responses, means for forming a second mathematical function of the ratio of the second and third responses, and means for combining the first and second functions to produce the output response.

25. Apparatus as in claim 24 wherein the first and second functions are substantially linear functions.

26. Apparatus as in claim 25 wherein the ratio of the first and second functions is formed in order to produce the output response.

27. Apparatus as in claim 24 wherein the first function is indicative of the number of terminal functional groups present in relation to the number of groups forming the backbones of the molecules, and wherein the second function is indicative of the number of groups forming the backbones of the molecules that have interacted with the radiations.

28. Apparatus as in claim 19 wherein the carbonaceous polymeric material is used to form a binder coating for the fibers in a mat of glass fibers, wherein the curing process includes exposing the mat to elevated temperatures, and wherein the exposed mat is passed through a measuring zone in which the radiations are directed into and received from the mat.

29. Apparatus as in claim 28 which comprises means for controlling the exposure of the mat to the elevated temperatures in accordance with the output response.

30. Apparatus as in claim 28 wherein the first infrared radiation comprises a near-infrared overtone band adapted to selectively interact with molecular resonance vibrations at one or both of the O—H and N—H vibration frequencies.

31. Apparatus as in claim 30 wherein the first infrared radiation has wavelengths in the vicinity of $1.50\mu$, and the second infrared radiation has wavelengths in the vicinity of $1.35\mu$ or $1.75\mu$.

32. Apparatus as in claim 30 or claim 31 which comprises means for directing into the mat a third infrared radiation which is different from the second radiation and which lies in a band of wavelengths in the vicinity of $1.35\mu$ or $1.75\mu$, means for producing from the received radiations a further response to the third infrared radiation, and means for producing the third response from the further response and the second response.

33. Apparatus as in claim 32 which comprises means for forming a first mathematical function of the ratio of the first and third responses, means for forming a second mathematical function of the ratio of the second and third responses, and means for combining the first and second functions to produce the output response.

34. Apparatus as in claim 33 wherein the first and second functions are substantially linear functions.

35. Apparatus as in claim 34 comprising means for forming the ratio of the first and second functions in order to produce the output response.

36. Apparatus as in claim 33 which comprises means for measuring the weight per unit area of the mat passing through the measuring zone, and means for controlling the rate of travel of the mat in accordance with the weight per unit area measurement, means for controlling the rate of application of the binder coating in accordance with the second mathematical function, and means for controlling the temperature of the mat during at least a portion of the curing process in accordance with the output response.

37. A method as in claim 1 which comprises producing from the first and second responses a fourth response that is indicative of the mass of the polymeric material interacting with the radiations but which is dependent on the variations in the absorptivity of the material for the first infrared radiation that occur as the curing process progresses, and utilizing the fourth response and the third response to produce the output response.

38. A method as in claim 37 wherein the fourth response is compensated for the radiation path length extension effects of radiation scattering.

39. A method as in claim 38 wherein the third response is similarly compensated for the effects of scattering.

40. A method as in claim 38 which comprises directing into the material further radiations having a mode of interaction with the material which is different from that of the infrared radiations, detecting the further radiations that have interacted with the material to produce an additional response, and using the additional response to effect the scattering compensation.

41. A method as in claim 40 wherein the further radiations are x rays or gamma rays.

42. A method as in claim 39 which comprises directing into the material further radiations having a mode of interaction with the material which is different from that of the infrared radiations, detecting the further radiations that have interacted with the material to produce an additional response, and using the additional response to effect scattering compensation of both the third and fourth responses.

43. A method as in claim 42 wherein the further radiations are x rays or gamma rays, and the third and fourth responses are similarly compensated.

44. A method as in claim 10 which comprises producing from the first and second responses a fourth response that is indicative of the mass of the polymeric binder material interacting with the radiations but which is dependent on the variations in the absorptivity of the binder material for the first infrared radiation that occur as the curing proces progresses, and utilizing the fourth response and the third response to produce the output response.

45. A method as in claim 44 wherein the fourth response is compensated for the radiation path length extension effects of radiation scattering by the binder-coated glass fibers.

46. A method as in claim 45 wherein the third response is similarly compensated for the effects of the scattering.

47. A method as in claim 46 which comprises directing x rays or gamma rays into the mat of glass fibers, detecting the x rays or gamma rays that have interacted with the mat of glass fibers to produce an additional response, and using the additional response to effect scattering compensation of both the third and fourth responses.

48. A method as in claim 47 wherein the additional response is additionally used to compensate the third and fourth responses for the infrared spectral effects of the glass in the fibers of the mat.

49. Apparatus as in claim 19 which comprises means for producing from the first and second responses a fourth response that is indicative of the mass of the polymeric material interacting with the radiations but which is dependent on the variations in the absorptivity of the material for the first infrared radiation that occur as the curing process progresses, and means for utilizing the fourth response and the third response to produce the output response.

50. Apparatus as in claim 49 comprising means for compensating the fourth response for the radiation path length extension effects of radiation scattering.

51. Apparatus as in claim 50 comprising means for similarly compensating the third response for the effects of scattering.

52. Apparatus as in claim 50 which comprises means for directing into the material further radiations having a mode of interaction with the material which is different from that of the infrared radiations, means for detecting the further radiations that have interacted with the material to produce an additional response, and means for using the additional response to effect the scattering compensation.

53. Apparatus as in claim 52 wherein the further radiations are x rays or gamma rays.

54. Apparatus as in claim 51 which comprises means for directing into the material further radiations having a mode of interaction with the material which is different from that of the infrared radiations, means for detecting the further radiations that have interacted with the material to produce an additional response, and means for using the additional response to effect scattering compensation of both the third and fourth responses.

55. Apparatus as in claim 54 wherein the further radiations are x rays or gamma rays, and the third and fourth responses are similarly compensated.

56. Apparatus as in claim 28 which comprises means for producing from the first and second responses a fourth response that is indicative of the mass of the polymeric binder material interacting with the radiations but which is dependent on the variations in the absorptivity of the binder material for the first infrared radiation that occur as the curing process progresses, and means for utilizing the fourth response and the third response to produce the output response.

57. Apparatus as in claim 56 comprising means for compensating the fourth response for the radiation path length extension effects of radiation scattering.

58. Apparatus as in claim 57 comprising means for similarly compensating the third response for the effects of the scattering.

59. Apparatus as in claim 58 which comprises means for directing x rays or gamma rays into the mat of glass fibers, means for detecting the x rays or gamma rays that have interacted with the mat of glass fibers to produce an additional response, and means for using the additional response to effect scattering compensation of both the third and fourth responses.

60. Apparatus as in claim 59 comprising means for utilizing the additional response to compensate the third and fourth responses for the infrared spectral effects of the glass in the fibers of the mat.

* * * * *